United States Patent [19]

Victor

[11] Patent Number: 4,508,928
[45] Date of Patent: Apr. 2, 1985

[54] ETHANOL EXTRACTION PROCESS

[75] Inventor: John G. Victor, Indian Head Park, Ill.

[73] Assignee: Institute of Gas Technology, Chicago, Ill.

[21] Appl. No.: 374,402

[22] Filed: May 3, 1982

[51] Int. Cl.$^3$ .............................................. C07C 29/86
[52] U.S. Cl. .................................... 568/916; 568/918
[58] Field of Search .............................. 568/916, 918

[56] References Cited

U.S. PATENT DOCUMENTS

| | | | |
|---|---|---|---|
| 1,524,192 | 1/1925 | Mann | 568/916 |
| 2,048,178 | 1/1936 | Carney | 202/41 |
| 2,080,064 | 5/1937 | Roelfsma | 202/39 |
| 2,081,721 | 5/1937 | Van Dijck et al. | 260/122 |
| 2,100,437 | 11/1937 | Engs et al. | 260/156 |
| 2,140,694 | 12/1938 | Evans | 202/42 |
| 2,196,177 | 4/1940 | Burk et al. | 260/639 |
| 2,510,806 | 6/1950 | Egberts et al. | 260/643 |
| 2,582,214 | 1/1952 | Twigg | 202/60 |
| 2,591,672 | 4/1952 | Catterall | 202/39.5 |
| 2,597,009 | 5/1952 | Lobo et al. | 260/450 |
| 3,455,664 | 7/1969 | Rosscup et al. | 568/918 |
| 4,261,702 | 4/1981 | Sweeney et al. | 568/916 |
| 4,306,884 | 12/1981 | Roth | 568/918 |
| 4,308,106 | 12/1981 | Mannfeld | 203/DIG. 4 |
| 4,349,415 | 9/1982 | DeFilippi et al. | 203/14 |

OTHER PUBLICATIONS

Othmer and Wentworth, "Absolute Alcohol—An Economical Method for Its Manufacture", Industrial & Engineering Chemistry, Dec. 1940, pp. 1588–1593.
Sherwood and Pigford, "Absorption and Extraction", 1952, pp. 391–392, 465.
Elgin and Weinstock, "Phase Equilibrium at Elevated Pressures in Ternary Systems of Ethylene and Water with Organic Liquids", J. Chem. and Engr. Data, vol. 4, No. 1, Jan. 1952, pp. 3–12.

Primary Examiner—J. E. Evans
Attorney, Agent, or Firm—Allegretti, Newitt, Witcoff & McAndrews, Ltd.

[57] ABSTRACT

A process for the separation of ethanol from water using solvent extraction at elevated pressures is disclosed. Separation is effected by contacting aqueous ethanol with either propylene (propene), allene (propadiene), methyl acetylene (propyne), or methyl allene (1,2-butadiene). This produces two liquid phases which separate because of the difference in their densities, and are easily drawn off as separate streams. The solvent is recovered by distillation and condensation using a heat pump to transfer heat. The ethanol and water remain in a liquid state and are substantially recovered.

7 Claims, 2 Drawing Figures

ETHANOL EXTRACTION PROCESS

BACKGROUND OF THE INVENTION

This invention relates to a solvent extraction process useful for the separation of ethanol from water, a principal benefit of which is a low energy requirement.

Certain specific processes which use solvent extraction to separate different organic liquids by selective solvent action are well-known in the art. For example, ethylene is used as a solvent to separate water-organic mixtures in J. C. Elgin and J. J. Weinstock, "Phase Equilibrium at Elevated Pressures in Ternary Systems of Ethylene and Water With Organic Liquids", J. Chem. and Engr. Data, Vol. 4, No. 1, January, 1959, pp. 3–12. However, ethylene has not been found to be an effective solvent for use in solvent extraction of such mixtures due to the low distribution coefficient of ethylene in water and organic liquid mixtures.

At present, solvents are used to separate ethanol from water only when very high concentrations (90–95% ethanol, by volume) of ethanol and water are involved, because ethanol forms an azeotrope with water at a concentration of about 95% ethanol, by volume, and distillation cannot increase the concentration of ethanol beyond this value. The use of benzene and ethyl ether in the extraction of absolute alcohol from an alcohol-water azeotrope is disclosed in D. F. Othmer and T. O. Wentworth, "Absolute Alcohol—An Economical Method for Its Manufacture", in Industrial and Engineering Chemistry, December, 1940, pp. 1588–1593.

Mann, U.S. Pat. No. 1,524,192 discloses the extraction of a high molecular weight alcohol, such as secondary butyl alcohol, from an aqueous solution, through the utilization of a hydrocarbon oil having a high initial boiling point, preferably above 325° F., as the solvent. Distillation is used to obtain the final dehydrated alcohol product.

In Carney, U.S. Pat. No. 2,048,178, a process for dehydrating organic compounds, such as secondary butyl alcohol, is disclosed. Olefin and parrafin hydrocarbons, such as pentane, isopentene and butane, which are substantially insoluble in water and soluble in the organic compound, are used as solvents. Carney utilizes steam in order to maintain process temperatures and to separate the solvent and organic compounds. This results in high energy costs. In addition, Carney fails to disclose the separation of ethanol from an aqueous medium through the utilization of his process and solvents.

In Van Dijck et al, U.S. Pat. No. 2,081,721, a process for separating a liquid mixture, containing one or more organic polar compounds, into two components or two groups of components, by solvent extraction, is disclosed. The process includes a washing step, in which the separated extract or solvent-rich phase is washed with a liquid stream of a nearly pure component. This process, like the process in Carney, is intended for use in the separation of water from an alcohol higher than ethanol, e.g., propyl and butyl alcohols, by using a hydrocarbon, such as pentane, as the extracting agent.

The feasibility of using solvent extraction as a substitute for distillation in alcohol separation and concentration was studied in J. W. Roddy, "Distribution of Ethanol—Water Mixtures to Organic Liquids", Ind. Eng. Chem. Process Des. Dev., Vol. 20, No. 1, 1981. All of the solvents studied were liquids at ambient temperature and atmospheric pressure.

The prior art separation processes heretofore developed for the separation of ethanol and water have process temperatures or solvent requirements which require large energy inputs and thus high energy costs. The present invention obviates the need for large energy inputs through the use of allene, methyl allene, propylene and methyl acetylene as solvents in a solvent extraction process.

By using these solvents, which are in the vapor state at ambient temperature and pressure, the energy required for their recovery, by distillation, from the ethanol or water can be supplied by exchange with the energy given up in their condensation. This exchange is brought about through the use of heat pumps, well-known devices which use pumping work to bring about heat transfer through efficient heat exchange.

SUMMARY OF THE INVENTION

It is an object of the present invention to provide a process for the separation of ethanol from water which is a less energy-intensive method than distillation.

A further object of the present invention is to provide a process to separate a liquid mixture of ethanol and water into at least two liquid streams or groups of liquid streams, one with a higher concentration of ethanol than the original mixture, the other with a lower concentration of ethanol.

It is a further object of the present invention to provide a process to separate ethanol from water which operates at conveniently low temperatures, thereby reducing the heating of large amounts of liquid.

An object of the present invention relates to a process for the separation of ethanol from water through the utilization of solvent extraction in which propylene (propene), allene (propadiene), methyl acetylene (propyne) or methyl allene (1, 2-butadiene) may be used as the liquid solvent.

In a principal aspect, the present invention relates to a process for the separation of ethanol from water through the utilization of solvent extraction with propylene (propene) being used as the liquid solvent. The process is performed by combining a liquid mixture containing ethanol and water and propylene. This produces two layers or phases, one enriched in ethanol and the other in water. The resulting layers are then separated. Vapor is subsequently evolved from each layer thereby leaving ethanol or water as separate liquids. In accordance with a preferred embodiment of the invention, no external source of heat is required to separate the solvent from the ethanol, because the solvent, itself, can supply, through compression and condensation, all the energy needed to maintain process temperatures. In this fashion, energy costs are minimized.

In an alternative aspect, the present invention relates to a process for the separation of ethanol from water through the utilization of solvent extraction with propylene (propene) being used as the liquid solvent. The process is performed by combining a liquid mixture containing ethanol and water and propylene. This produces two layers or phases, a solvent phase enriched in ethanol and an aqueous phase. The resulting layers separate by virtue of their difference in density. Solvent is subsequently evolved from each layer, preferably by distillation, brought about by the addition of heat, thereby leaving ethanol or water as separate liquids. This heat is supplied from the heat given up upon condensing the solvent, through a heat pump device. In this manner, energy costs are minimized.

These and other objects, advantages and features of the invention will be set forth in the detailed description which follows.

BRIEF DESCRIPTION OF THE DRAWING

In the detailed description which follows, reference will be made to the drawing comprised of the following figures.

DESCRIPTION OF THE PREFERRED EMBODIMENT

In general terms, the present invention relates to a means for separating ethanol from water by solvent extraction. A liquid mixture containing at least ethanol and water is contacted with a liquid solvent, which is, preferably, propylene (propene), but may also be allene (propadiene), methyl acetylene (propyne) or methyl allene (1, 2-butadiene), to produce a liquid mixture containing separate layers. The layers are then drawn off, and are thus separated. The top layer contains solvent which must be recovered. The bottom layer will contain a small amount of solvent, unless the solvent is propylene, which also must be recovered. Propylene is sufficiently insoluble in water that it need not be recovered from the water-rich lower layer, which makes it especially attractive for use in the process. Solvent recovery and the production of an ethanol stream having an enriched ethanol content is effected by utilizing a low-temperature distillation technique which causes the liquid solvent to vaporize and thus separate from the liquid ethanol product. Energy for this distillation is provided by the heat given up by the solvent vapor in condensing to liquid.

A more detailed explanation of the process is set forth with reference to FIG. 1, which is a schematic flow diagram of a preferred embodiment of the process.

Figure 1:
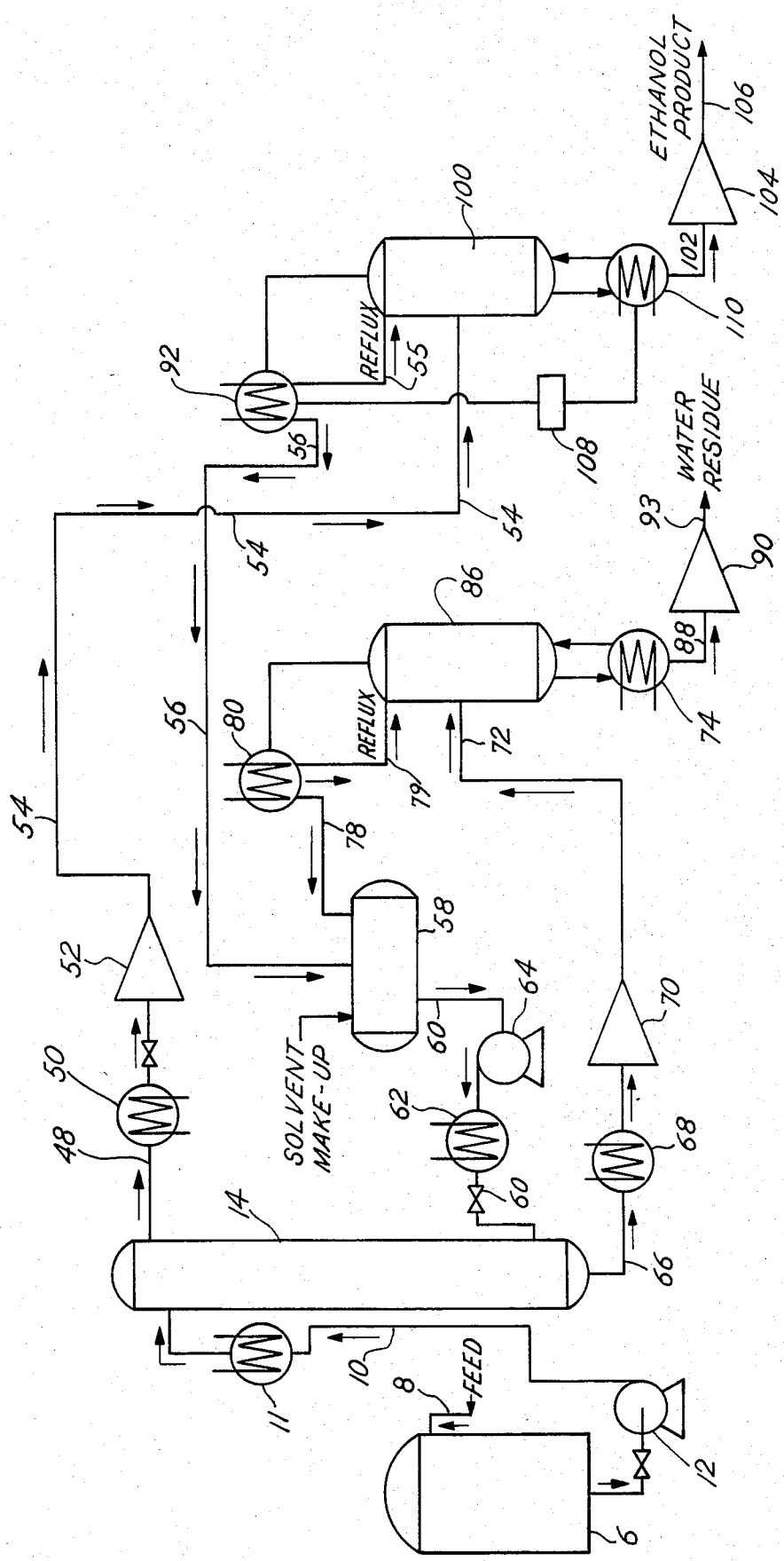
FIG. 1 is a schematic flow diagram illustrating a preferred embodiment of the disclosed process.

In a preferred embodiment of the present invention, as in FIG. 1, a mixture containing ethanol and water, as received from feed line 8, is stored in an ethanol storage vessel 6.

The mixture is pumped, through line 10, by a pump 12, from vessel 6 through a heat exchanger 11 which increases its temperature, and into a solvent extractor separation vessel 14. Solvent, which is, preferably, propylene, but may also be allene, methyl acetylene or methyl allene, is introduced, via line 60, into the solvent extractor 14 from a solvent storage vessel 58. Prior to being introduced into the solvent extractor 14, the liquid solvent is pumped by a pump 64 through a heat exchanger 62.

In the solvent extractor 14, the solvent and the aqueous ethanol are mixed to produce a lighter, solvent-rich, ethanol enriched layer or phase, and a heavier, water-rich, ethanol-depleted phase. The two phases are drawn off separately from solvent extractor 14, via lines 48 and 66, respectively. The separation of the ethanol from water is achieved by:

(1) The ability of the solvent to dissolve some ethanol, but little, if any, water;

(2) The amount of contact, or interfacial surface area, between solvent and the ethanol-water mixture; and (3) The difference in the densities between light and heavy layers, which allows them to separate.

The heavier, water-rich layer and especially the lighter, ethanol-enriched layer each contain some solvent which should be recovered and recycled unless propylene is used as solvent. In such a case, recovery of propylene from water is unnecessary. Typically, the recovery of solvent from ethanol and the production of an ethanol-enriched product is conveniently carried out in a pressurized distillation column 100. Upon leaving the solvent extractor 14, via line 48, the lighter, ethanol-enriched stream passes through a heat exchanger 50 and a turbine 52, which lower the temperature and pressure, respectively, of the stream. The stream then passes, via line 54, through a reboiler 110, which adds heat to the liquid stream, containing solvent and ethanol, leaving the bottom of the distillation column 100 sufficient to vaporize all the solvent. The solvent vapor stream is returned to the distillation column 100, where it contacts liquid falling down the column 100, thereby stripping the solvent. The vapor containing solvent issues from the top of the column 100, into a condenser 92. Some condensed solvent may be returned to the distillation column 100, as reflux via line 55. Within the distillation column 100, the feed stream descends and contacts slightly superheated solvent vapor. This vapor, introduced to the base of the column 100 and effervescing upward, acts to vaporize the liquid solvent. It exits from the top of column 100.

The condenser 92 removes enough heat to transform the saturated vapor to a liquid. This heat is transferred to the reboiler 110, utilizing a device known as a heat pump 108.

The condensed solvent is pumped to a higher pressure and recycled, via line 56, to the solvent storage tank 58. The ethanol-enriched product stream will contain only a trace of solvent, which can be recovered, if desired, by undergoing a second distillation at a lower pressure. The ethanol product stream flows out of the bottom of the reboiler 110, via line 102, and passes through a turbine 104, which lowers the pressure of the ethanol. The resulting ethanol product issues from the process via line 106.

Solvent recovery from the water-rich layer proceeds in the same fashion as its recovery from the ethanol-enriched product stream. Upon leaving the solvent extractor 14, via line 66, the water-rich stream passes through a heat exchanger 68 and a turbine 70, which lower the temperature and pressure, respectively, of the stream. The stream then passes through a reboiler 74 which adds heat to the liquid stream, containing solvent and water, leaving the bottom of the distillation column 86 sufficient to vaporize all the solvent. The solvent vapor stream is returned to the distillation column 86, where it contacts liquid falling down the column 86, thereby stripping the solvent. The solvent vapor issues from the top of the column 86, into a condenser 80. Some condensed solvent may be returned to the distillation column 86, as reflux via line 79. The condenser 80 removes enough heat to transform the saturated solvent vapor into a saturated liquid. This heat is transferred to the reboiler 74, through the use of heat pump 76. The condensed solvent is then returned, via line 78, to the solvent storage tank 58. The returned solvent may be cooled, if desired, through the use of a heat exchanger, to eliminate frictional heat added by the heat pump 76 and other pumps.

The water stream flows out of the bottom of the reboiler 74, via line 88, and passes through a turbine 90, which lowers the pressure of the water. The water is then removed from the process via line 93.

It may be desirable to operate the solvent extraction vessel 14 at a higher temperature than that of the distillation columns, 86 and 100, used for solvent recovery. This can conveniently be brought about by adding heat to the liquid solvent and also to be ethanol feed stream to the solvent extraction vessel 14. This heat can be supplied from the heat recovered in reducing the temperature of the ethanol-enriched solvent stream and the water-rich stream leaving the extraction vessel 14 from heat exchangers 50 and 68, respectively. The heat transfer also may utilize a heat pump, although an alternative would be to heat the entering streams directly and cool the streams leaving the solvent extractor 14 through direct heat exchange between the feed streams.

The present invention can be better understood with reference to the following examples:

ILLUSTRATIVE EXAMPLE I

Figure 2:
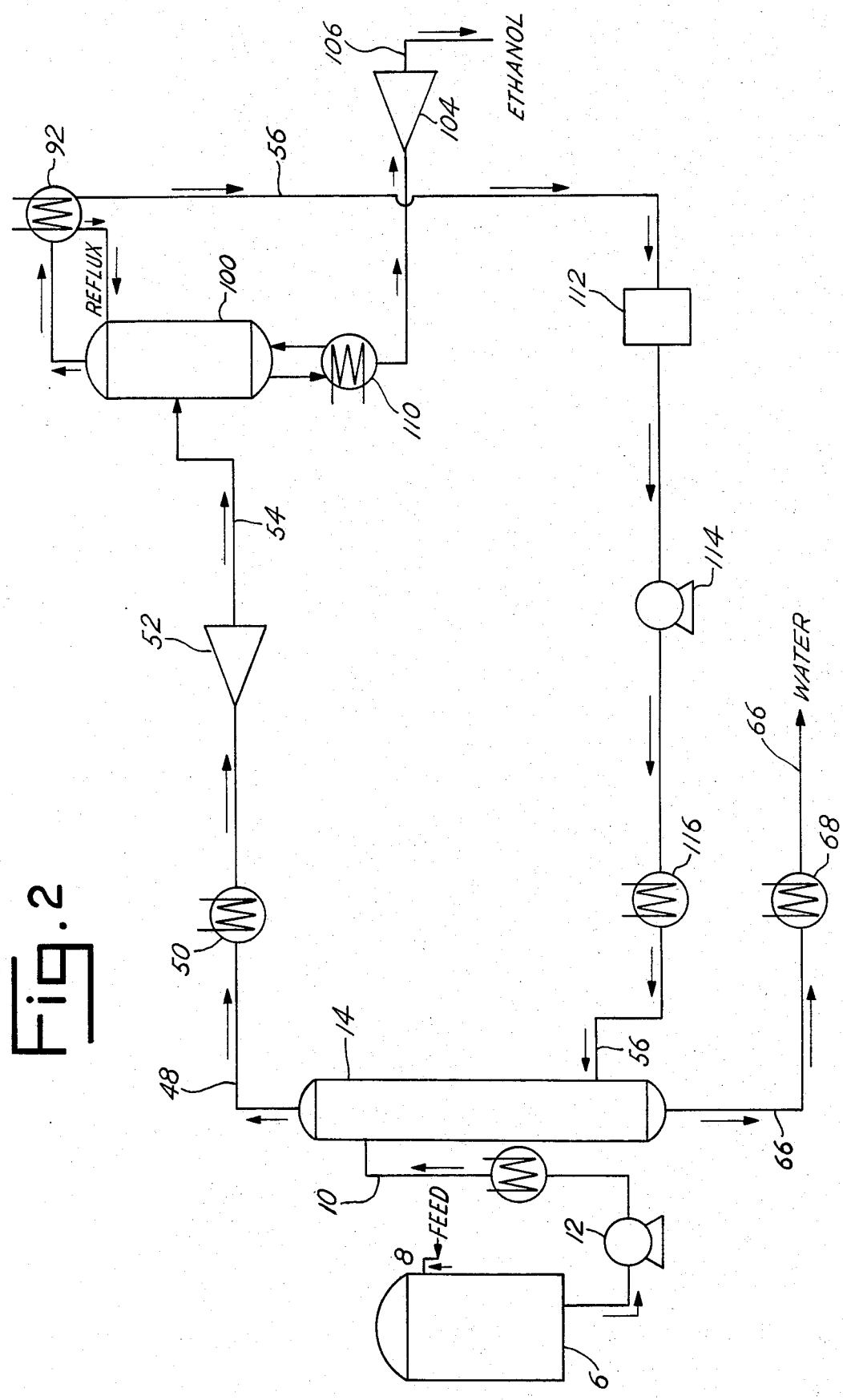
FIG. 2 is a schematic flow diagram illustrating the ethanol extraction process using propylene as the liquid solvent.

With reference to FIG. 2, a schematic flow diagram illustrating a specific ethanol extraction process using propylene as the liquid solvent is illustrated. The following descriptive flow rates are proportional to flow rates which could be utilized in the process, and are based upon experimental tests and evaluations.

100 lbs/hr. of a mixture, containing 5% by weight ethanol and 95% by weight water at a temperature of 20° C. and a pressure of 1 atm. (absolute), is pumped through line 10, to a heat exchanger 11 which increases its temperature to 60° C. It then enters a solvent extractor separation vessel 14. Vessel 14 is maintained at a temperature of 60° C. and a pressure of 375 psia. 540 lbs/hr. of propylene, at a temperature of 60° C. and a pressure of 372 psia. are then introduced into the solvent extractor 14, via line 56, to provide contact with the ethanol and water.

The solvent extractor 14 should be of a height, for this example, sufficient to provide 60 equilibrium stages. The height of an equilibrium stage will vary depending upon the type of packing, or internal trays, inside the extractor. It will also vary to a certain extent with the velocity of propylene flowing through it. In any event, this velocity of propylene must be less than that which would cause the extractor to "flood," that is, entrain water with the propylene leaving at the top.

In the continuous counter-current solvent extractor 14 of this example (other types may also be utilized), the aqueous ethanol descends as small droplets through a rising liquid stream of propylene. Sixty equilibrium stages allow the production of a substantially water-free, light, ethanol-rich layer containing 0.92% ethanol and 99.08% propylene. The heavier, water-rich layer contains only trace amounts of ethanol and propylene. The light layer is removed at a rate of 545 lbs/hr., the heavy layer, at 95 lbs/hr. The 95 lbs/hr. of water leaving the solvent extraction vessel 14 enters, via line 66, a heat exchanger 68 which reduces its temperature prior to its leaving the process.

The propylene-ethanol stream flows, via line 48, to a heat exchanger 50, reducing its temperature to 20° C. Some work may be recovered by allowing the liquid stream, under a pressure of 371 psia., to flow through a hydraulic turbine 52, thus reducing the pressure of the stream to 147 psia., at 20° C.

The propylene-ethanol stream travels, via line 54, to a distillation column 100 maintained at a pressure of 140 psia. Ethanol-free solvent vapor leaves at the top of the column 100, and the liquid feed descends from the feed point enriched in ethanol and leaves at the bottom of the column 100.

The propylene present in the ethanol leaving the column 100 is removed by heating in the reboiler 110 and is returned to the column 100 as slightly superheated propylene vapor. The 5 lb/hr. of ethanol product stream leaves the reboiler 110, via line 106, at 20° C. after having its pressure reduced to 14.7 psia. in a hydraulic turbine 104.

The 540 lbs/hr. of propylene vapor issuing from the distillation column 100 flows to a condenser 92, maintained at 139 psia. and 20° C., where sufficient heat is removed to condense the propylene vapor. The liquid stream then flows to a surge vessel 112 where any needed make-up propylene is added to it. 540 lbs/hr. of liquid propylene are pumped, by pump 114, to a pressure of 376 psia. and flow into a heat exchanger 116. The temperature of the propylene is increased from 20° C. to 60° C. in the heat exchanger 116, and is returned, via line 56, to the solvent extraction vessel 14.

ILLUSTRATIVE EXAMPLES II–IV

The same process, as in Example I, was designed, except that allene, methyl acetylene and methyl allene were used, respectively, in EXAMPLES II–IV, instead of propylene, as solvents.

The design results are summarized in TABLE I.

TABLE I

| Example | Solvent Used | Amount of Solvent Used in Solvent Extractor | Amount of Mixture of Ethanol and Water Used (Initially 5 Weight % Ethanol in Water) | Temperature (°C.) of Solvent Extractor | Pressure (PSIA) in Solvent Extractor |
|---|---|---|---|---|---|
| II | Allene (Propadiene) | 560 lb/hr. | 100 lb/hr. | 80 | 384 |
| III | Methyl Acetylene (Propyne) | 560 lb/hr. | 100 lb/hr. | 80 | 318 |
| IV | Methyl Allene (1,2-butadiene) | 560 lb/hr. | 100 lb/hr. | 80 | 126 |

| Example | Temperature (°C.) of Distillation Column | Pressure (PSIA) Necessary For Condensation of Solvent | Amount of Ethanol Separated From Water | Amount of Ethanol Recovered From Distillation Column | Amount of Solvent Recovered From Distillation Columns |
|---|---|---|---|---|---|
| II | 20 | 102 | approaching 100% depending on number of stages | 5 lb/hr. | 560 lb/hr. |
| III | 20 | 66 | approaching 100% | 5 lb/hr. | 560 lb/hr. |

TABLE I-continued

| | | | | | |
|---|---|---|---|---|---|
| | | | depending on number of stages | | |
| IV | 20 | 21 | approaching 100% depending on number of stages | 5 lb/hr. | 560 lb/hr. |

The pressure at which the solvent extraction process of the present invention can be operated is the vapor pressure of the solvent at the temperature of extraction. Pressures less than 400 psia are desirable from the standpoint of vessel design. Typical temperatures at which the solvent extraction can be operated are in a range of 20° C. up to the critical temperature of the solvent, with 60° C. to 80° C. being a desirable range between higher ethanol distribution coefficients and higher pressure. Typical temperatures at which the distillation step is performed are from 20° C. to 80° C., with 20° C., or ambient temperature, being preferred. Typical pressures at which the distillation step is performed correspond to the vapor pressure of the solvent at the temperature of the distillation, typically around 150 psia. The ratio of solvent to liquid contacted in the extraction step is a function of the amount of alcohol contained in the liquid mixture and the degree of separation desired and is readily ascertainable by one skilled in the art. Typical ratios of the amount of solvent used to the amount of liquid mixture used, on a volume basis, range from 8 to 11, depending on the solvent, with 11 being preferred for greater ethanol recovery.

The process of the present invention can produce alcohol of approximately 100% by weight purity in a single, multi-stage extraction column. It also permits recovery of up to 100% by weight of the alcohol originally present in the liquid mixture fed to the column. A single operating stage can produce alcohol of approximately 100% by weight purity, but will permit recovery of only about 40% by weight of the alcohol originally present in the liquid mixture.

The solvents of the present invention, namely, propylene (propene), allene (propadiene), methyl acetylene (propyne) and methyl allene (1, 2-butadiene), when used for solvent extraction, lead to a successful ethanol extraction, which has low energy requirements because the solvents are far easier to separate from ethanol than ethanol is from water.

It should be understood that the foregoing disclosure emphasizes certain specific embodiments of the invention and that all modifications or alternatives equivalent thereto are within the spirit or scope of the invention as set forth in the appended claims.

I claim as my invention:

1. A process for extracting ethanol from an aqueous solution containing ethanol which comprises contacting the solution with propylene (propene) solvent at conditions of pressure and temperature sufficient to maintain the solvent in the liquid state, and to selectively extract at least a portion of the ethanol from the solution and to provide two separate liquid phases including a solvent phase containing the extracted ethanol.

2. A process as in claim 1 which further comprises recovering solvent from at least one of the liquid phases in a distillation column by adding heat to said distillation column through the use of heat pump means, said heat causing said solvent to evaporate, thereby forming solvent vapor, and to condense.

3. A process for extracting ethanol from an aqueous solution containing ethanol which comprises contacting the solution with a solvent selected from the group consisting of propylene (propene), allene (propadiene), methyl acetylene (propyne) and methyl allene (1, 2-butadiene) at conditions of pressure and temperature sufficient to maintain the solvent in the liquid state, and to selectively extract at least a portion of the ethanol from the solution and to provide two separate liquid phases including a solvent phase containing the extracted ethanol.

4. A process as in claim 3 which comprises recovering solvent from at least one of the liquid phases in a distillation column by adding heat to said distillation column through the use of heat pump means, said heat causing said solvent to evaporate, thereby forming solvent vapor, and to condense.

5. A process for the extraction of ethanol from a liquid mixture of ethanol and water comprising the steps of:

(a) combining the liquid mixture with liquid solvent selected from a group consisting of propylene (propene), allene (propadiene), methyl acetylene (propyne), and methyl allene (1, 2-butadiene) to produce two phases, one phase being solvent and ethanol-rich, and the other being water-rich;

(b) separating the ethanol and solvent-rich phase from the water-rich phase, thereby forming separate liquid streams, one stream being ethanol and solvent-rich, and the other being water-rich;

(c) distilling the ethanol and solvent stream, thereby evaporating the solvent in a distillation column; and, (d) recovering the solvent as liquid in a condenser, thereby generating said heat, said heat being transferred to said distillation column through a heat pump means.

6. A process as in claim 5 wherein said liquid solvent is propylene (propene).

7. A process as in claim 5 wherein said liquid solvent is selected from a group consisting of allene (propadiene), methyl acetylene (propyne), and methyl allene (1, 2-butadiene).

* * * * *